United States Patent
Holzapfel et al.

(10) Patent No.: US 8,123,994 B2
(45) Date of Patent: *Feb. 28, 2012

(54) METHOD OF MAKING CATHETER INCLUDING A UNIBODY DISTAL GUIDEWIRE PORT

(75) Inventors: Mark S. Holzapfel, Cedar, MN (US); Martin J. Plantenberg, Rogers, MN (US); Daniel K. Tomaschko, Savage, MN (US); Richard J. Olson, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/644,898

(22) Filed: Dec. 22, 2009

(65) Prior Publication Data

US 2010/0096077 A1   Apr. 22, 2010

Related U.S. Application Data

(63) Continuation of application No. 10/653,375, filed on Sep. 2, 2003, now Pat. No. 7,662,328.

(51) Int. Cl.
*B29C 65/02* (2006.01)
*A61M 25/16* (2006.01)
*A61M 25/09* (2006.01)
*A61M 25/10* (2006.01)

(52) U.S. Cl. .................... 264/248; 604/96.01
(58) Field of Classification Search .............. 264/248
See application file for complete search history.

(56) References Cited

U.S. PATENT DOCUMENTS

| | | | |
|---|---|---|---|
| 4,670,009 A | 6/1987 | Bullock |
| 5,091,205 A | 2/1992 | Fan |
| 5,135,535 A | 8/1992 | Kramer |
| 5,156,594 A | 10/1992 | Keith |
| 5,306,247 A | 4/1994 | Pfenninger |
| 5,342,301 A | 8/1994 | Saab |
| 5,360,330 A | 11/1994 | Jensen et al. |
| 5,380,301 A | 1/1995 | Prichard et al. |
| 5,395,335 A | 3/1995 | Jang |
| 5,501,667 A | 3/1996 | Verduin, Jr. |
| 5,522,818 A | 6/1996 | Keith et al. |
| 5,554,118 A | 9/1996 | Jang |
| 5,690,613 A | 11/1997 | Verbeek |
| 5,817,053 A | 10/1998 | Agarwal |
| 5,824,173 A | 10/1998 | Fontirroche et al. |
| 5,876,375 A | 3/1999 | Penny |
| 5,947,927 A | 9/1999 | Mertens |
| 5,980,486 A | 11/1999 | Enger |

(Continued)

FOREIGN PATENT DOCUMENTS

JP    09-276411 A    10/1997

(Continued)

*Primary Examiner* — Christina Johnson
*Assistant Examiner* — Patrick Butler
(74) *Attorney, Agent, or Firm* — Seager, Tufte & Wickhem, LLC

(57) ABSTRACT

Methods and devices incorporating a guidewire entry port subassembly for use in rapid exchange catheters. The use of a subassembly allows for stronger quality control and simpler fabrication of a rapid exchange device. In several embodiments, methods of making a molded guidewire entry port using a mold, often in conjunction with one or more mandrels, are disclosed. Several device embodiments include a separate molded guidewire port as well as molded guidewire ports which are attached, during a molding step, to segments of a catheter.

20 Claims, 10 Drawing Sheets

U.S. PATENT DOCUMENTS

| | | |
|---|---|---|
| 6,030,369 A | 2/2000 | Engelson et al. |
| 6,066,100 A | 5/2000 | Willard et al. |
| 6,106,487 A | 8/2000 | Duane et al. |
| 6,143,013 A | 11/2000 | Samson et al. |
| 6,190,358 B1 | 2/2001 | Fitzmaurice et al. |
| 6,193,685 B1 | 2/2001 | Goodin |
| 6,319,229 B1 | 11/2001 | Kim et al. |
| 6,344,029 B1 | 2/2002 | Estrada et al. |
| 6,346,093 B1 | 2/2002 | Allman et al. |
| 6,361,529 B1 | 3/2002 | Goodin et al. |
| 6,368,302 B1 | 4/2002 | Fitzmaurice et al. |
| 6,409,863 B1 | 6/2002 | Williams et al. |
| 6,475,187 B1 | 11/2002 | Gerberding |
| 6,503,223 B1 | 1/2003 | Sekido et al. |
| 6,520,951 B1 | 2/2003 | Carrillo, Jr. et al. |
| 6,554,795 B2 | 4/2003 | Bagaoisan et al. |
| 7,662,328 B2 * | 2/2010 | Holzapfel et al. ............ 264/248 |

FOREIGN PATENT DOCUMENTS

| | | |
|---|---|---|
| WO | 99/44667 A1 | 9/1999 |

* cited by examiner

METHOD OF MAKING CATHETER INCLUDING A UNIBODY DISTAL GUIDEWIRE PORT

RELATED APPLICATIONS

This application is a continuation of co-pending U.S. application Ser. No. 10/653,375, filed Sep. 2, 2003, the entire disclosure of which is incorporated herein by reference.

FIELD OF THE INVENTION

The present invention is related to medical devices, more particularly to elongate medical devices such as catheters. In particular, the present invention is related to catheters which have a distal guidewire port.

BACKGROUND OF THE INVENTION

Single-operator-exchange (SOE) or "monorail" catheters are catheters in which only a distal portion of the catheter tracks over a guidewire. Proximal of the distal portion that tracks the guidewire, an SOE catheter and guidewire are separate from one another. This allows the proximal portion of the SOE catheter to be relatively simple, having need of one less lumen than would be required for an over-the-wire catheter that tracks a guidewire over its entire length. An SOE catheter is also useful because, by not tracking the guidewire over its entire length, the catheter and guidewire are more easily moved relative one another, such as during a catheter exchange. One example of an early patent in this area is U.S. Pat. No. 5,156,594 to Keith, the disclosure of which is incorporated by reference.

A drawback for SOE catheters is the difficulty of fabrication. Construction of an SOE device typically involves welding or fusing several lengths of tubing together such that a distal portion of the SOE device includes an additional lumen for receiving a guidewire. A guidewire opening or port is provided to allow a guidewire to be introduced to the guidewire lumen through the guidewire port. A number of different manners for providing the guidewire port joint to a rapid exchange-type of medical device have been suggested, for example, by Fitzmaurice et al., U.S. Pat. No. 6,190,358; Enger, U.S. Pat. No. 5,980,486; Estrada et al., U.S. Pat. No. 6,344,029, and Williams et al., U.S. Pat. No. 6,409,863. Williams et al. is also hereby incorporated by reference. The disclosure of the Keith patent above, incorporated by reference, discloses a crimped hypotube which is then attached to a distal polymer member having a guidewire tube and an outer tube around the guidewire tube.

The steps of preparing (including, for example, crimping, trimming or cutting), placing and fusing the tubular members in proper alignment are labor intensive, creating costs in terms of labor, time and quality assurance. This is particularly so given the small size of the various pieces of the final SOE product.

SUMMARY OF THE INVENTION

The present invention provides a number of methods for providing guidewire port subassembly for use in a catheter, as well as a number of pieces for using in assembling a catheter. A number of combinations are provided in a number of embodiments, where none or one or more of the proximal, distal guidewire or distal outer tubular members may be fused to the port subassembly during fabrication of the port subassembly.

A first embodiment includes a method of making a catheter comprising providing a port joint for coupling a proximal member to one or more distal members, the port joint adapted to couple a lumen in the proximal member to a lumen defined by the distal member(s). For the illustrative method, port joint includes a guidewire port for receiving a guidewire and a guidewire lumen for coupling the guidewire into a lumen defined by said distal member(s).

In several embodiments, a method of providing a port joint subassembly for a rapid exchange catheter is provided. The method includes molding a port joint subassembly for joining a proximal member having a first lumen to a distal member having a second lumen and a distal guide member having a guidewire lumen, the port joint subassembly adapted to couple the first lumen to the second lumen and including a guidewire port for directing a guidewire from outside the catheter into the guidewire lumen. In several illustrative embodiments, the port joint subassembly may be attached to one or more of the proximal member, the distal member or the distal guide member during fabrication. The attachment may be accomplished by providing a portion of one or more of the proximal member, the distal member or the distal guide members inside a mold used to shape the port joint subassembly in an injection molding process. In further embodiments, the port joint subassembly may be provided with structures adapted to receive or attach to the proximal member, the distal member or the distal guide member.

One embodiment comprises a port joint subassembly adapted to couple to a proximal member and two distal members. Several embodiments encompass devices including molded port joint subassemblies. In one such embodiment, the device includes a proximal member for providing an inflation fluid which is attached to a port joint subassembly by molding the port joint with over the proximal member to create an attachment between the two. The proximal member may be inserted to a mold for shaping the port joint subassembly and some portion of the port joint subassembly molded around the proximal member. The proximal member may also be inserted to a mold for shaping the port joint subassembly and some portion of the port joint subassembly allowed to flow into the proximal member to create attachment from the interior of the proximal member. A combination of inner and outer attachment may also be provided as desired. Additional embodiments include provision of a distal guide member and distal member in like fashion as that just explained with respect to the proximal member.

Further embodiments include methods for providing strain relief across a port joint subassembly by molding the port joint subassembly and providing for attachment to a strain relief member such as a core wire, a coil, or a spiral cut portion of a hypotube, or any other strain relief structure. The attachment may be provided adhesively, or the chosen strain relief structure may be provided using a specially shaped mold for the port joint subassembly. In another embodiment, the strain relief member may be placed at least partly within a mold for making the port joint subassembly such that attachment is achieved during a molding step.

DETAILED DESCRIPTION OF THE PREFERRED EMBODIMENTS

The following detailed description should be read with reference to the drawings. The drawings, which are not necessarily to scale, depict illustrative embodiments and are not intended to limit the scope of the invention. Throughout the following description, a to number of molds are described. The molds may be made of any suitable material and may be provided with any of a variety of known coatings for aiding in a molding process. Further, while not shown, the molds can include any of the known types of injection ports allowing for injecting a molding material as well as any desired venting ports. Single or multiple infusion/vent ports may be used in a single mold, and the mold may be fabricated by any of a number of known processes with a wide variety of materials, without altering the inventive concepts described herein.

Figure 1:
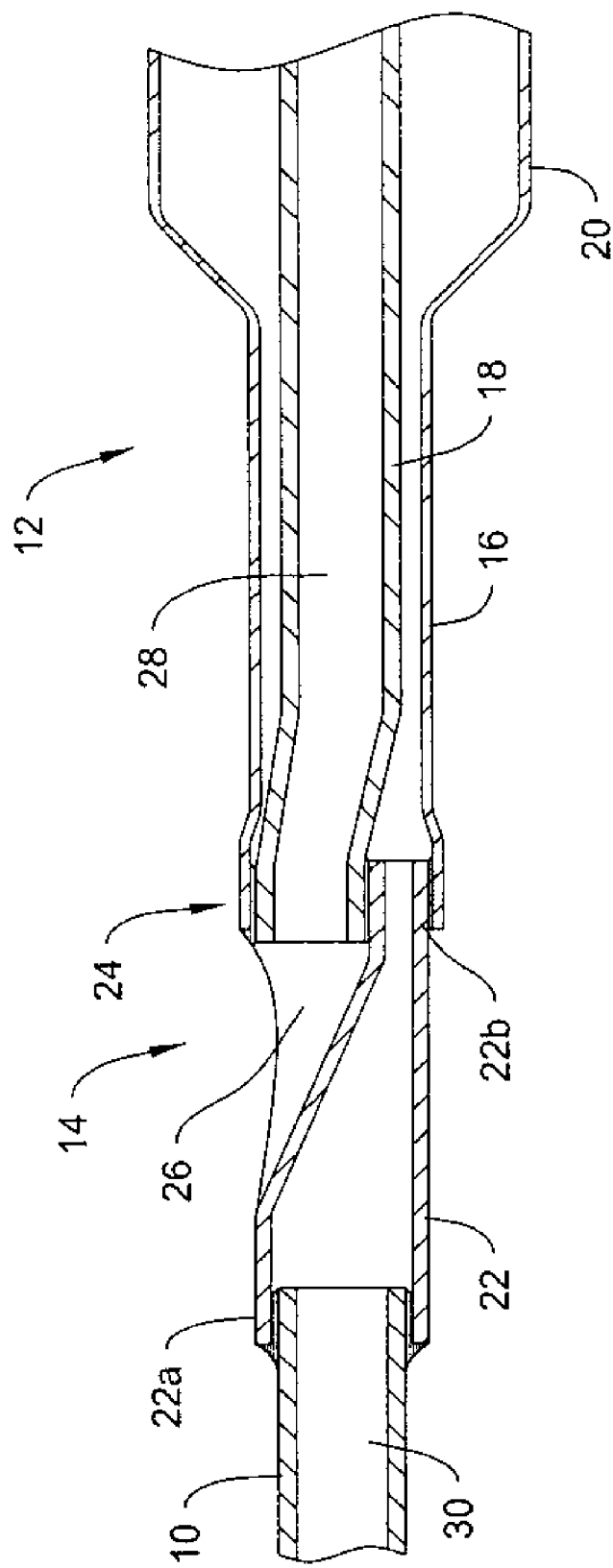
FIG. 1 is a cross-sectional view of a prior art distal guidewire port.

FIG. 1 is a cross-sectional view of a prior art distal guidewire port. A similar port is illustrated in U.S. Pat. No. 5,156,594. The sectional view shows a midshaft region where a proximal member 10 is joined to a distal member 12 across a port joint 14. The distal member 12 includes an outer member 16 and an inner member 18. The outer member 16 defines a generally annular lumen around the inner member 18. The outer member 16 may couple to an inflatable member 20. The port joint 14 includes a midshaft member 22 having a proximal end 22a and a distal end 22b.

The midshaft member 22 is disposed so that, at its proximal end 22a, it is generally circular and surrounds and is attached to the proximal member 10. At the distal end 22b, the midshaft member 22 takes on a crescent shape, partially surrounding the inner member 18 on one side, with the outer member 16 surrounding both the midshaft member 22 and the inner member 18. It is readily observed that forming the joint 24 at the distal end 22b of the midshaft member 22 can be time consuming and labor intensive.

During this process, of course, care must be taken to form a suitable entry 26 for a guidewire to pass into the guidewire lumen 28 defined by the inner member 18. Additional care must also be taken to preserve the integrity, and keep open, the inflation lumen 30 which passes from the interior of the proximal member 10 to the midshaft member 22 and into the outer member 16 of the distal member 12. Difficulty can arise due to the use of a tubular midshaft member 22 between the proximal member 10 and the distal member 12, as the midshaft member 22 must be carefully shaped and held in place.

Figure 2:
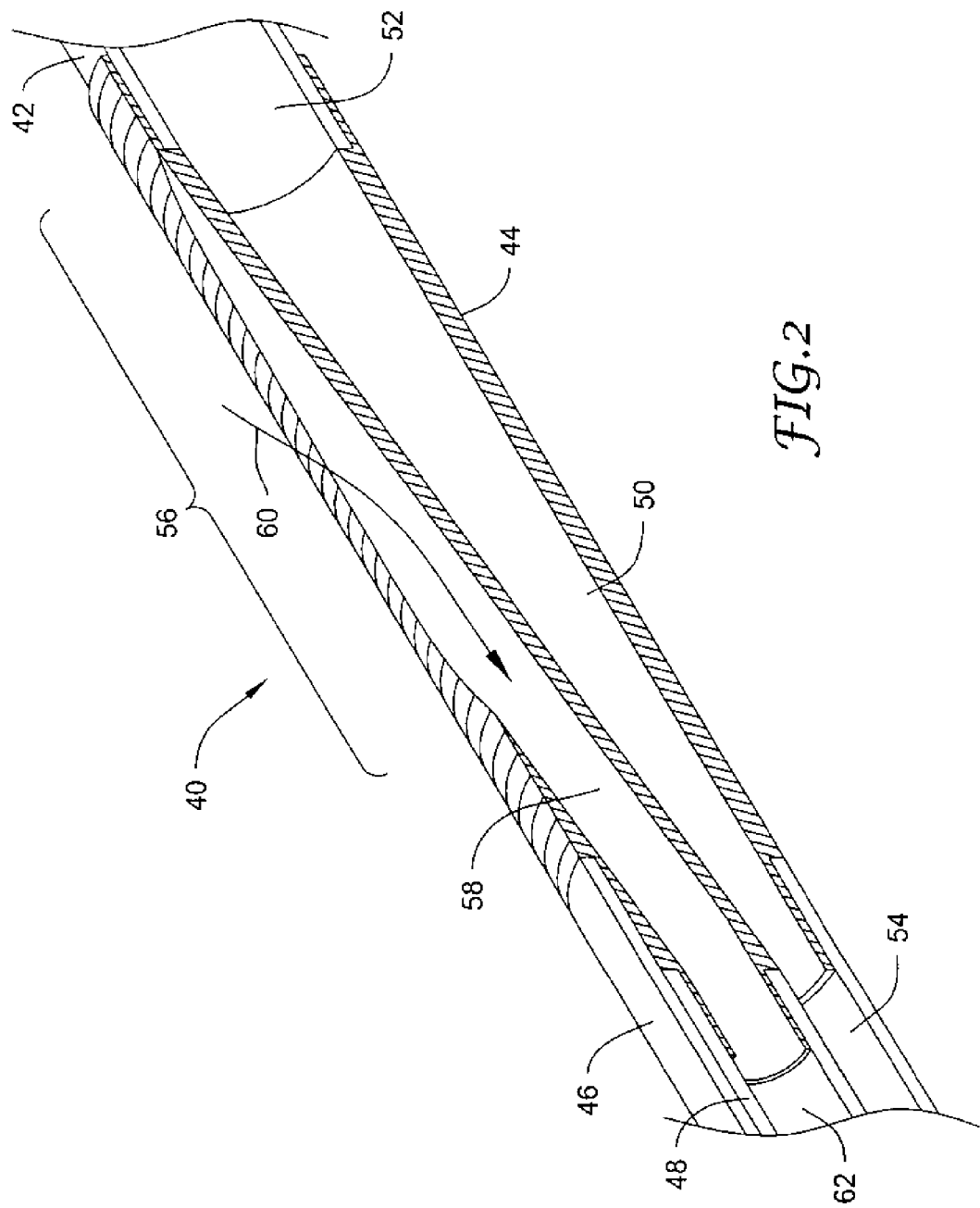
FIG. 2 is a partial cut-away perspective view of a distal guidewire port in accordance with an illustrative embodiment of the present invention.

FIG. 2 is a partial cut-away perspective view of a distal guidewire port in accordance with an illustrative embodiment of the present invention. A midshaft portion 40 of an assembled rapid exchange catheter is illustrated, including a proximal member 42 coupled to a port joint 44, which in turn couples to a distal outer member or shaft 46 and a distal inner member or shaft 48. The port joint 44 of the illustrative embodiment is constructed by use of a molding process.

The port joint 44 is shaped to include several features. A passageway 50 provides an inflation lumen connecting a first inflation lumen 52 defined by the proximal member 42 with a second inflation lumen 54 defined between the distal outer shaft 46 and the distal inner shaft 48. An opening 56 allows access to a guidewire passage 58 that connects to the guidewire lumen 62 of the distal inner shaft 48. A ramped portion 60 allows for a relatively smooth entry for the guidewire into the guidewire passage 58.

One or more of the proximal member 42, distal outer shaft 46 and distal inner shaft 48 may be attached to the port joint 44 during fabrication of the port joint 44 itself. For example, the proximal member 42 may be inserted into a mold used to make the port joint 44 prior to injecting molding material, and, due to the heat and other effects of the process, the port joint 44 and proximal member 42 can become affixed to one another as the injected material cools. In another example, the distal outer member 46 may be partially inserted into a mold used to make the port joint 44 prior to injection, and again, the distal outer member 46 and the port joint 44 can become affixed to one another as the injected material cools. Likewise, the distal inner member 48 may be partially inserted into a mold used to make the port joint 44 prior to injection, and the distal inner member 48 can become affixed to the port joint 44 as the injected material cools.

In further embodiments, more than one of the proximal member 42, distal outer shaft 46, or distal inner shaft 48 may be affixed to the port joint 44 in similar fashion during a molding step. In one such embodiment, the heat occurring during the molding step can cause the distal outer member 46 and distal inner member 48 to become affixed to one another, providing additional strength to the midshaft portion 40, particularly where the proximal member 42 is stiffer than either distal member 46, 48. In other embodiments a butt joint, rather than the lap joints illustrated, may be used.

Alternatively, a port joint may be fabricated independently. For example, an injection molding process, where molten injectate material is infused into a mold, may be used. Alternatively, the port joint may be machined by taking a piece of material (i.e. a polymer) and drilling holes and grinding the exterior to achieve the desired shape and configuration of lumens and member receiving locations.

Any suitable material, such as a polymer, may be used for constructing the port joint 44. Some suitable polymers and coatings include the following polymers and copolymers: polycarboxylic acid polymers and copolymers including polyacrylic acids (e.g., acrylic latex dispersions and various polyacrylic acid products; acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polybismaleinimides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); anhydride polymers and copolymers including maleic anhydride polymers; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the same.

Several embodiments make use of polyether block amides (PEBAX) for the port joint 44. Some illustrative factors to consider in selecting a suitable material for the port joint 44 include consideration of the compatibility with the materials of the adjacent tubular members (i.e., the proximal member 42, the distal outer member 46 and the distal inner member 48) as well as final product properties such as tensile strength, pushability, lubricity and flexibility. The material may be chosen to provide a transition in flexibility or other characteristics between the proximal member 42 and the distal members 46, 48. In some embodiments, additional features may be used to provide enhanced or different properties including, for example, the provision of a core wire that may be placed through the port joint during the fabrication process to improve strain relief or pushability, or a heat shrink member that may be placed about the port joint to improve lubricity or tensile strength. Coatings or other treatments may also be applied.

Several of the following embodiments illustrate methods for providing a distal port subassembly or transition section. Included are embodiments illustrating attaching a proximal member or either distal member to a port joint during a molding step, as well as an embodiment where each of the proximal member and both distal members are attached simultaneously during a molding step. Various combinations of these attachment techniques may also be used.

Figure 3A:
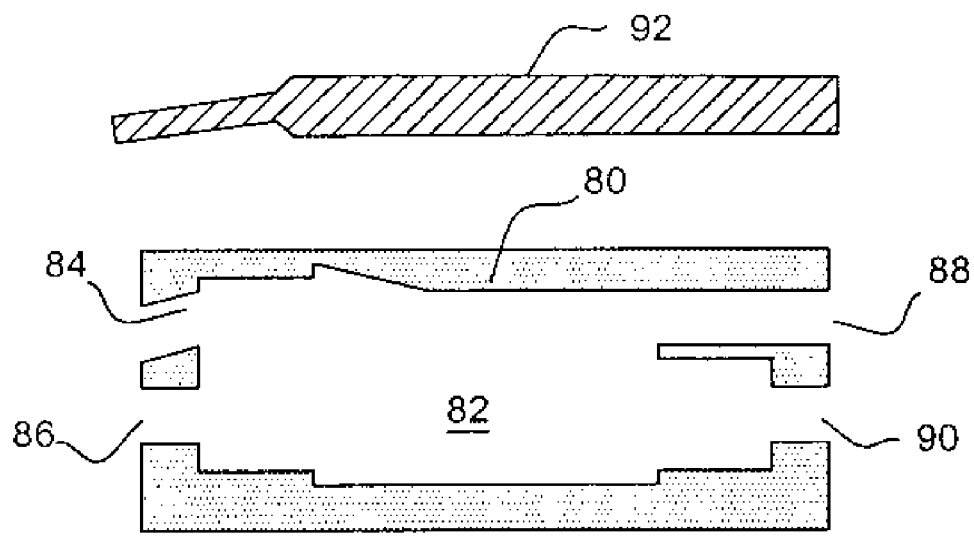
FIGS. 3A-3D are cross-sectional views showing steps of an illustrative embodiment including a distal inner section attached during a molding step.

FIGS. 3A-3D are cross-sectional views showing steps for use of an illustrative embodiment including a distal inner section attached during a molding step. FIG. 3A illustrates two specialized parts for the process. A mold 80 is shown in cross section. The mold 80 defines a volume 82 having a number of openings including a distal guide opening 84, a distal inflation opening 86, a proximal mandrel opening 88, and a proximal inflation opening 90. Also used is a guide path mandrel 92 having a somewhat curved distal end having a lesser diameter.

Figure 3B:
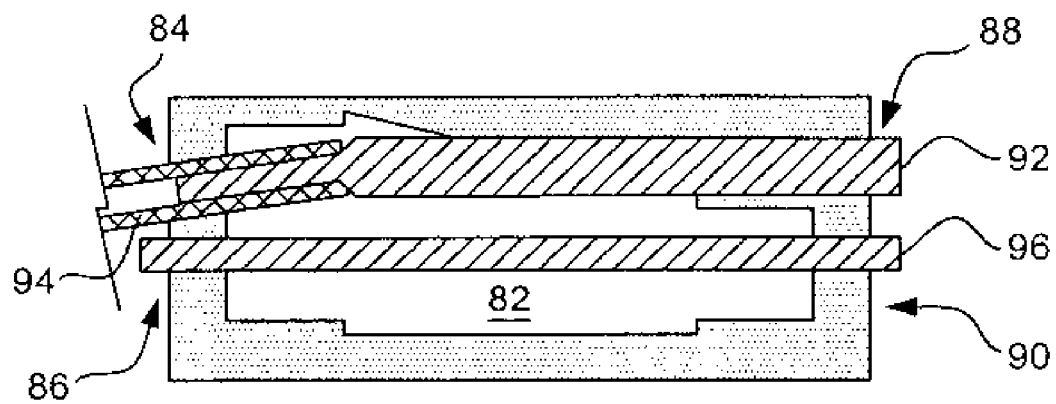

FIG. 3B illustrates a pre-mold configuration for the mold 80 having the guide path mandrel 92 inserted. Prior to insertion of the guide path mandrel 92, the narrow end of the guide path mandrel 92 was loaded onto the proximal end of the distal inner member 94. This combination is loaded into the mold 80 such that the guide path mandrel 92 extends from the proximal mandrel opening 88 and the distal inner member 94 extends from the distal guide opening 84. An inflation mandrel 96 (so named here to indicate it maintains an inflation lumen opening) is placed to pass through the distal inflation opening 86 and the proximal inflation opening 90. While FIG. 3B is a cross-sectional view, it should be understood that the volume 82 extends around the mandrels 92, 96 and the distal inner member 94 to create a three-dimensional space for injecting a molding material. Once configured as in FIG. 3B, a molding material is injected to the volume 82 by any suitable process.

Figure 3C:
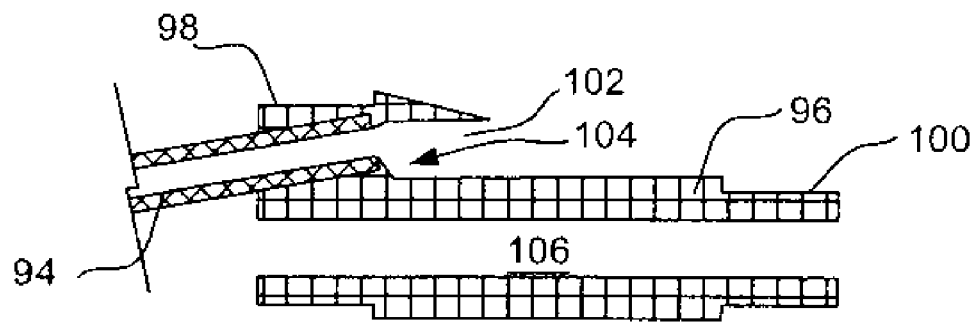

After the molding step, the mold and mandrels are removed to leave an apparatus or catheter sub-assembly as illustrated in cross section in FIG. 3C having the distal inner member 94 and a port joint subassembly 96 attached together. Selection of compatible materials for the distal inner member 94 and the port joint subassembly 96 will result in attachment of the port joint subassembly 96 to the distal inner member 94 during the molding step.

Because of the shape of the mold, the port joint subassembly 96 includes several to locations adapted for attachment to other catheter parts. This includes a distal attachment location 98 which may be a collar or smoothed region sized to receive a distal outer member (not shown). The distal attachment location 98 may also include a ridge such that it can slidably receive a distal outer member (not shown) up to a controlled location, assuring repeatable engagement of a distal outer member (not shown) to the distal attachment location 98.

A proximal attachment location 100 is also illustrated. The proximal attachment location 100 may be adapted in to allow for engagement of a proximal member (not shown) and may include features similar to those of the distal attachment location 100. Either attachment location may also be provided with mechanical attachment features such as, for example, a locking collar having a ridge, threading, barbs or other mechanical features.

The guide path mandrel 92 (FIG. 3B) is removed to leave a guidewire entry port 102 including a smoothed entry location 104. The guide wire entry port 102 leads into the lumen defined by the distal inner member 94. The combination of the guide wire entry port 102, smoothed entry location 104 and inner member 94 create a guidewire entry path. By using the fabrication methods illustrated herein, the guidewire entry path of FIG. 3C can be shaped as desired, without requiring special treatment (i.e., slitting, skiving or the like) of a tubular member. This allows for improved entry path features and reduced production costs. If desired, the guidewire entry port 102 may be machined for further definition of the entry path. The inflation mandrel 96 (FIG. 3B) is removed to leave an inflation lumen 106 which is designed to allow inflation fluid (and hence inflation pressure) to pass from a proximal member to a distal member.

Figure 3D:
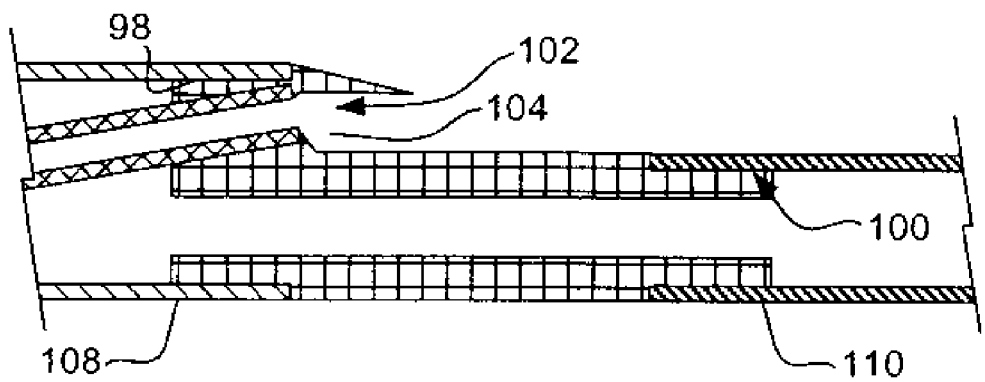

FIG. 3D illustrates in cross section a port joint incorporating the device of FIG. 3C. In particular, a distal outer member 108 has been provided in a location to correspond to the distal attachment location 98. In one embodiment the distal outer member 108 is attached at the attachment location by the use of either a hot jaw or a laser bonding process, either of which creates localized heating, melting and attachment. In other embodiments an adhesive, mechanical lock or any other suitable process may be used to attach the distal outer member. Also, a proximal member 110 is attached at the proximal attachment location 100. Again, the attachment may be by the use of localized heating, adhesive, mechanical or any other suitable process. Further embodiments may also include various strain relief members placed across or incorporated into the port joint, including a spiral cut hypotube, a coil member, or the like.

Figure 4A:
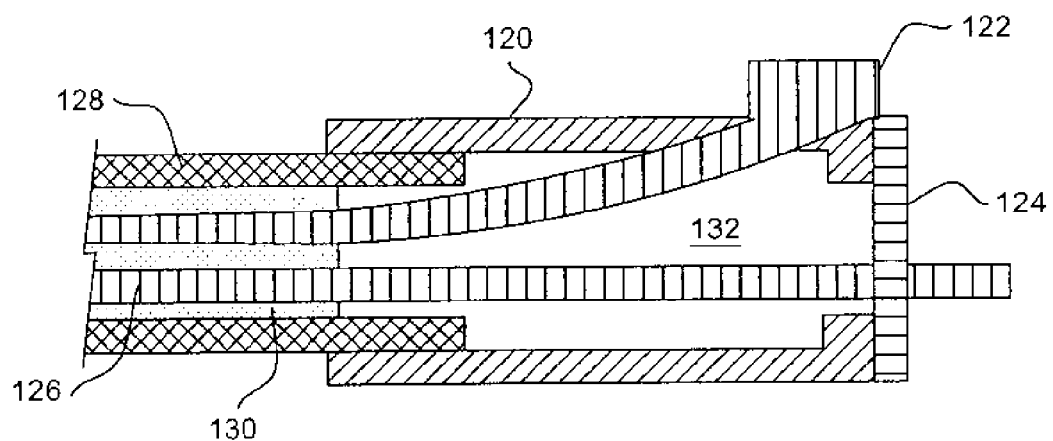
FIGS. 4A-4D are cross-sectional views showing steps of an illustrative embodiment including a distal outer section attached during a molding step.

FIGS. 4A-4D are cross-sectional views showing steps of an illustrative embodiment including a distal outer section attached during a molding step. FIG. 4A illustrates a configuration in a pre-molding step. A mold 120 is provided with a guide path mandrel 122, a proximal cap 124, and an inflation mandrel 126. The guide path mandrel 122 and inflation mandrel 126 may include mechanisms for securing to the mold 120 and proximal cap 124, respectively. The proximal cap 124 is removably secured to the mold 120.

A distal outer member 128 is shown partially inserted into the mold 120. Though not shown, the mold 120 may include a stop or other feature for preventing the distal outer member 128 from being passed too far into the mold. An injection stop 130 is also illustrated, the injection stop 130 having been placed over the distal ends of the mandrels 122, 126. The injection stop 130 may be placed first and the distal outer member 128 slid thereover, or the injection stop may be loaded into the distal outer member 128 and then loaded over the mandrels 122, 126.

In one embodiment, the injection stop 130 is sized to match the desired length of the distal outer member 128, and one of the mandrels 122, 126 may include a taper or other feature such that the injection stop 130 may only pass a certain distance over whichever mandrel 122, 126 is so designed. Thus, by observing the distal end of the distal outer member 128 with respect to the distal end of the injection stop 130, one may achieve a repeatable placement of the distal outer member 128 with respect to the mold 120. The distal outer member 128 may also be constructed of a transparent material to facilitate observation of the positioning of the injection stop 130. The injection stop 130 aids in containment of the injectate material (which is typically in a liquid-like form) to a space 132 defined by the mold 120 and cap 124, the mandrels 122, 126, and the distal outer member 128.

Figure 4B:
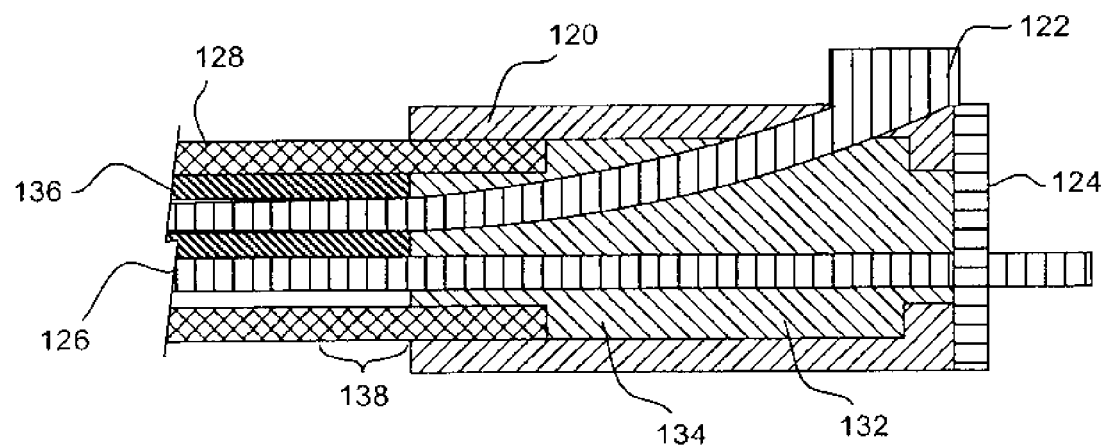
Figure 4C:
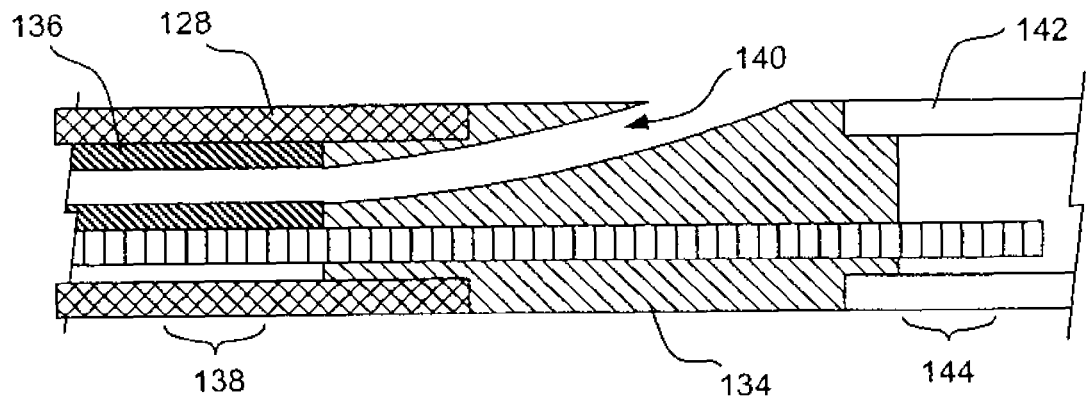

After the configuration of FIG. 4A is achieved, a suitable material is injected to the mold 120 and allowed to cool/solidify to form a shaped member 134 in the space 132, as shown in FIG. 4B. The injection stop 130 (FIG. 4A) is then removed. A distal inner member 136 is passed over the guide path mandrel 122 until it reaches an attachment location 138 adjacent the member 134. The distal inner member 136, at least near its proximal end (the end illustrated on FIG. 4B), is then attached along the attachment location 138 to at least one of the distal outer member 128 or the member 134. Such attachment may be achieved by any of a number of methods including, for example, the application of localized heating (i.e., a hot jaw, laser bonding, or welding process) at the attachment location 138. Any suitable heating, mechanical or adhesive process may also be used.

In one embodiment, the guide path mandrel 122 may be a member including a lumen at least partially therethrough, with an opening at a location corresponding to the proximal end of the distal inner member 136, and an adhesive may be infused through the guide path mandrel 122 to the attachment location 138 for attaching the distal inner member 136. Although the device illustrated shows the distal inner member 136 shifted to one side of the distal outer member 128, more distal portions may allow the distal inner member 136 to be centered, or may maintain the distal inner member 136 to one side.

The mold 120 and proximal cap 124 may be removed before or after the distal inner member 136 is attached. In several embodiments the guide path mandrel 122 may remain in place to maintain a desirable, smooth guide path entry during heating used in some embodiments to attach the distal inner member 136. After attachment of the distal inner member 136, the guide path mandrel 122 may be removed, opening the guidewire entry port 140 of the member 134, the shape of which is generally controlled by the shape of the guide path mandrel 122. The inflation mandrel 126 may remain in place as a proximal member 142 is placed to engage a proximal attachment location 144. The proximal member 142 is, in an illustrative embodiment, attached at the proximal attachment location 144 by the application of localized heat. In other embodiments, the proximal attachment location 144 may include mechanical features for attaching the proximal member 142, or an adhesive may be applied. If heat is used, the guide path mandrel 122 and/or the inflation mandrel 126 may remain in place to maintain the patency of the lumens defined by each against the applied heat.

Figure 4D:
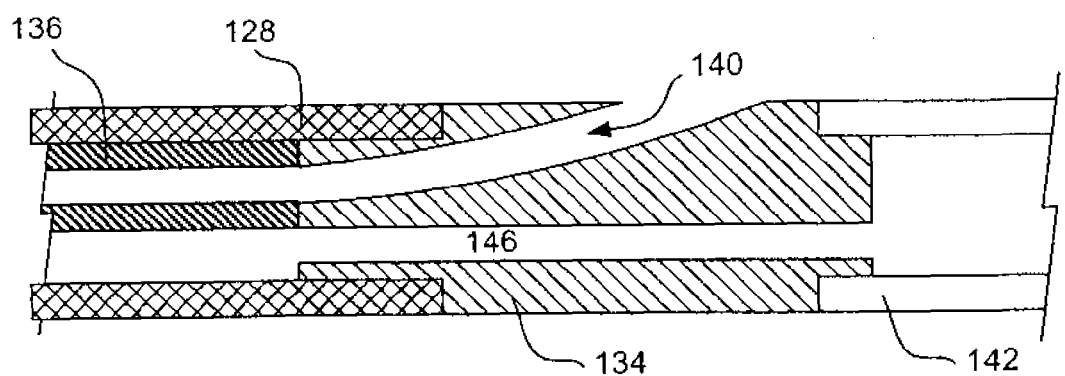

FIG. 4D illustrates a completed joint, with the inflation mandrel removed to illustrate an inflation lumen 146 defined by the member 134. The inflation lumen 146 connects a lumen defined by the proximal member 142 to a lumen defined between the distal outer member 128 and the distal inner member 136. It should be noted that in contrast to the illustrative embodiment of FIGS. 3A-3D, the illustrative embodiment of FIG. 4D has a relatively constant diameter across the port joint. Either form may be achieved with the present invention.

In the illustrative embodiment of FIGS. 4A-4D, the inflation mandrel 126 is loaded through the distal outer member 128. This may improve ease of fabrication, since the inflation mandrel 126 would need to be only a few centimeters longer than the distal outer member 128, which is typically relatively short in comparison with the proximal member 142. To allow for a relatively short inflation mandrel 126, the injection stop 130 may be provided with a slit along a side thereof allowing the inflation mandrel 126 to be held in place at a distal end while the injection stop 130 is removed and peeled off of the inflation mandrel 126.

FIGS. 5A-5D are cross-sectional views showing steps of an illustrative embodiment including each of the distal outer and distal inner sections, as well as the proximal member, being attached during a molding step. A mold 160 includes a proximal guide opening 162, a proximal inflation opening 164, and a distal opening 168, and defines a space 170. A distal outer member 172 is inserted partially into the mold 160. The distance of insertion may be controlled mechanically if desired, while in at least one embodiment a visible marker may be supplied on the distal outer member 172 to indicate proper insertion.

Figure 5A:
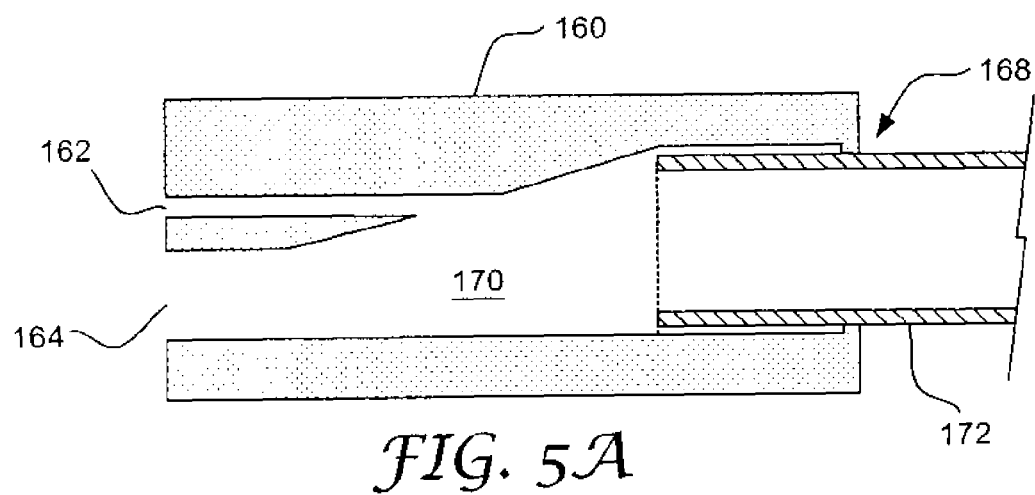
FIGS. 5A-5D are cross-sectional views showing steps of an illustrative embodiment including each of the distal outer and distal inner sections, as well as the proximal member, being attached during a molding step.
Figure 5B:
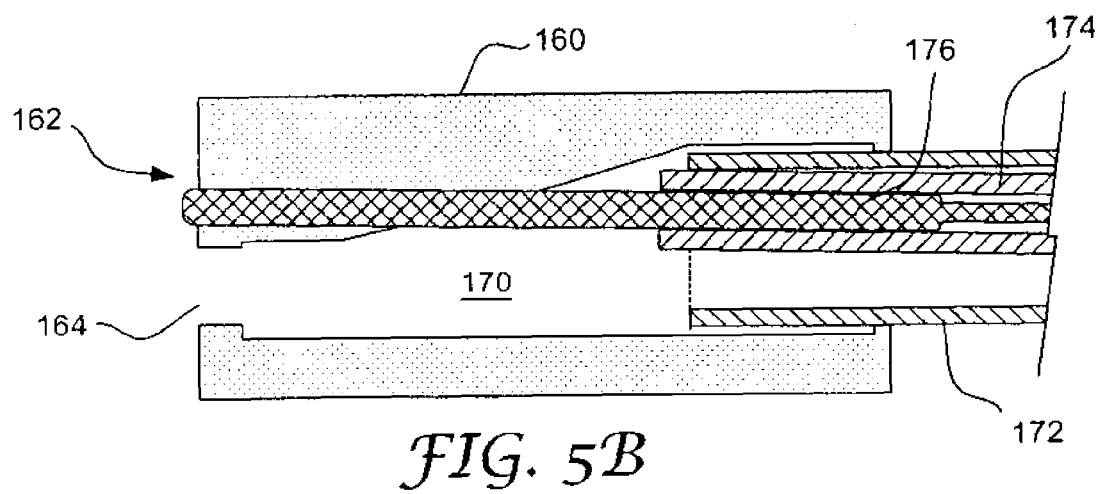

FIG. 5B illustrates a next step in the preparation of the mold 160. A distal inner member 174 is illustrated as including a guide mandrel 176 loaded at least partially therein, passing through the space 170 and out of the mold 160. The guide mandrel 176 may be sized to fittingly slide into the distal end of the distal inner member 174 and may be tapered to allow easy removal. The guide mandrel 176 need not be full length with respect to the distal inner member, and may, in fact, be substantially shorter as further explained below. As placed, the guide mandrel 176 extends out of the proximal guide opening 162.

Figure 5C:
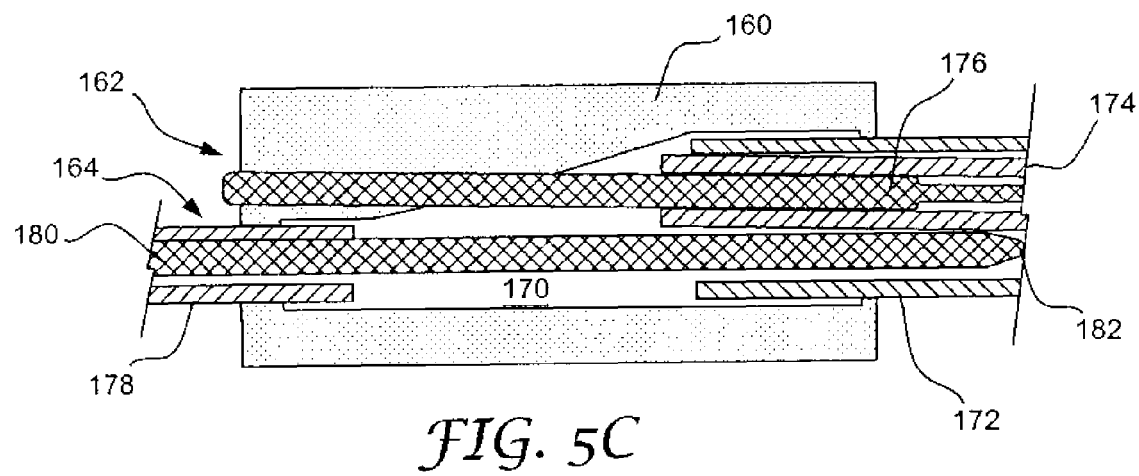

Next, as shown in FIG. 5C, a proximal member 178 is partially inserted to the mold 160 in a fashion similar to that of the distal outer member 172. The proximal member 178 is also pre-loaded with an inflation mandrel 180, although in an alternative embodiment, the inflation mandrel 182 may be pre-loaded to the distal outer member 172 and the distal end of the proximal member 178 loaded thereon. The inflation mandrel 180 passes through the space 170 and the mold 160, and includes a taper 182 to allow easy passage into space between the distal outer member 172 and the distal inner member 174. The space 170 is shaped to create a space outside of each of the inserted members 172, 174, 178, which will allow molding material to pass around the inserted members 172, 174, 178, creating attachment thereto.

Figure 5D:
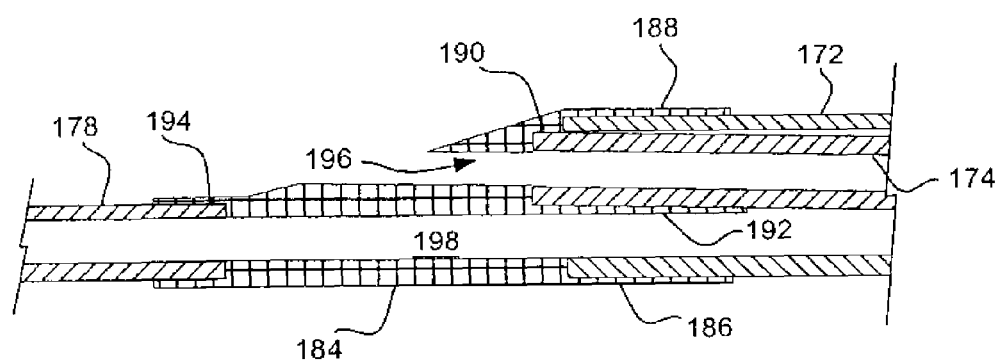

FIG. 5D is a cross section illustrating the structure formed after molding is performed with the configuration shown in FIG. 5C to create a member 184. The mold 160 (FIG. 5C) and mandrels 176, 182 (FIG. 5C) have been removed. As illustrated, the distal outer member 172 is now attached to the member 184 at a first outer location 186 and a second outer location 188, where the member 184 surrounds a portion of the distal outer member 172. Any ridges at these locations may be smoothed by, for example, grinding, provision of a shrink tube, or by a heating step that results in minor plastic re-flow.

The distal inner member 174 is attached to the member 184 at an outer location 190 as well as along an inner extension 192. The inflation mandrel (not shown) may be specially shaped to encourage creation of an attachment along an inner extension 192. The proximal member 178 is also attached along a location 194. Again, any flare or edges created at these attachment locations may be smoothed by any appropriate steps, including grinding, laser removal or localized re-melt.

A guidewire entry port 196 is created and leads into the distal inner member 174. The actual shape and any other characteristics of the guidewire entry port 196 are readily adjusted and controlled by shaping of the guide mandrel (not shown) and the distal guide port (not shown) of the mold (not shown). The distal inner member 174 is illustrated as being at an angle with respect to the distal outer member 172, which may allow for a coaxial distal section defining an annular inflation lumen. The angle may also create an easy passage for a guidewire to traverse with little friction.

The member 184 also defines an inflation lumen 198 which fluidly connects a lumen defined by the proximal member 178 to a lumen defined between the distal inner member 174 and the distal outer member 172. The inflation lumen 198 may be of any chosen shape, as controlled by the shape of the inflation mandrel.

As noted, the process illustrated in FIGS. 5A-5D allows the molding step to create an attachment to each of the proximal member 178 and both distal members 172, 174. This may allow for a simpler fabrication process or may create more consistent bonds among the several elements of the final design. Such fabrication processes, where an injectate material is injected such that it contacts another part of the final product are sometimes referred to as insert molding processes.

Figure 6A:
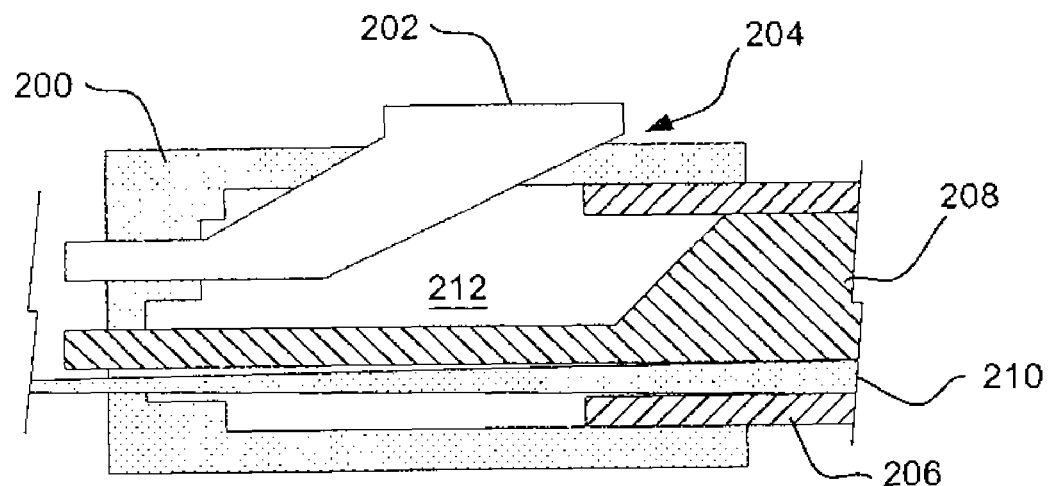
FIGS. 6A-6D are cross-sectional views showing steps of an illustrative embodiment including the proximal member attached during a molding step.

FIGS. 6A-6D are cross-sectional views showing steps of an illustrative embodiment including the proximal member attached during a molding step. FIG. 6A illustrates a configuration prepared for a molding step. A mold 200 is provided with a guide mandrel 202 which may be attached thereto. A proximal opening 204 of the mold 200 has a portion of a proximal member 206 inserted therein. An inflation mandrel 208 extends within the proximal member 206 and has a specially formed distal end. A core wire 210, which may be tapered as shown or may have a cylindrical, stepped or other shape, is placed to extend from a location proximal of the area shown to a location distal of the area shown. For example, the core wire 210 may be attached to the proximal member 206 using an adhesive or by a spot weld (if, for example, the proximal member 206 is a hypotube). Also, if a hub is provided on the proximal member 206, the core wire 210 may be snap fit to or into the hub. The core wire 210 passes through a volume 212 where a molding material will be infused. The mold 200 includes distal openings for receiving the guide mandrel 202, inflation mandrel 208 and core wire 210.

Figure 6B:
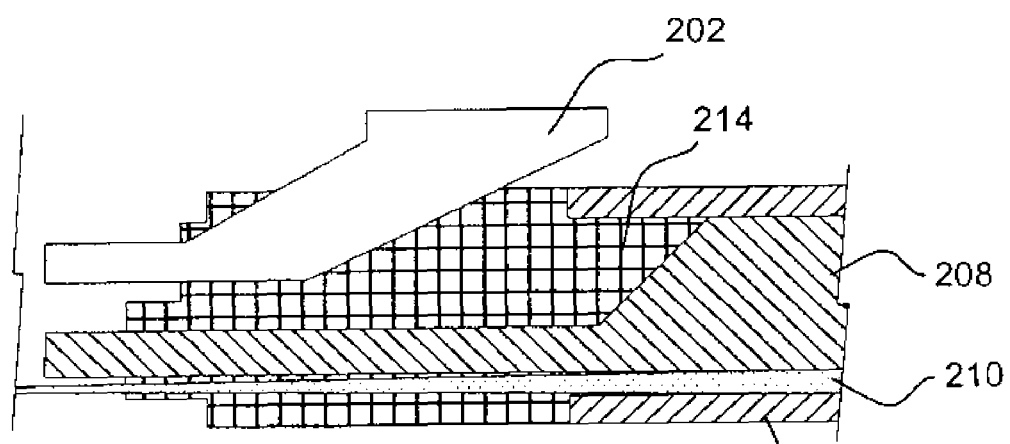

FIG. 6B illustrates a device as fabricated by injecting a material in the mold 200 of FIG. 6A. As illustrated, the mold 200 has been removed. The member 214 is shown having the guide mandrel 202 passing through a first portion, as well as being attached to the proximal member 206 and surrounding in part the core wire 210. During the molding process, the core wire 210 may or may not become securely attached (i.e., adhered to) the member 214, depending on the materials used for both pieces and any intervening coatings or other factors. The inflation mandrel 208 is also shown remaining in place.

Figure 6C:
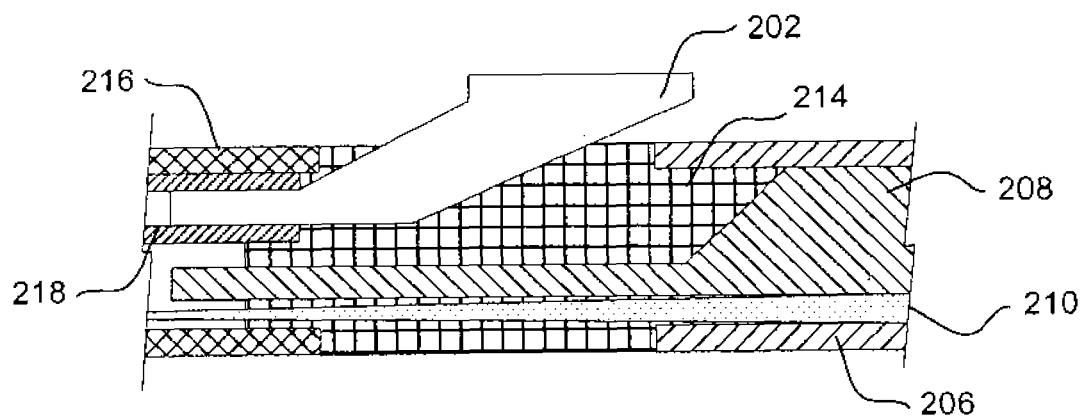

Once the configuration shown in FIG. 6B is achieved (and, if desired, the injected material is properly cooled), additional parts may be added if desired, as shown in FIG. 6C. In particular, a distal outer member 216 is placed over a portion of the member 214, while a distal inner member 218 is placed about the tip of the guide mandrel 202. The guide mandrel 202 may be left in place for the purpose of guiding the distal inner member 218 to the proper alignment and location as shown. With the distal outer member 216 and distal inner member 218 placed, a localized heating process may be used to create attachment with the member 214 and between the two distal members 216, 218. Alternatively, an adhesive or mechanical structure may be used to create an attachment.

Figure 6D:
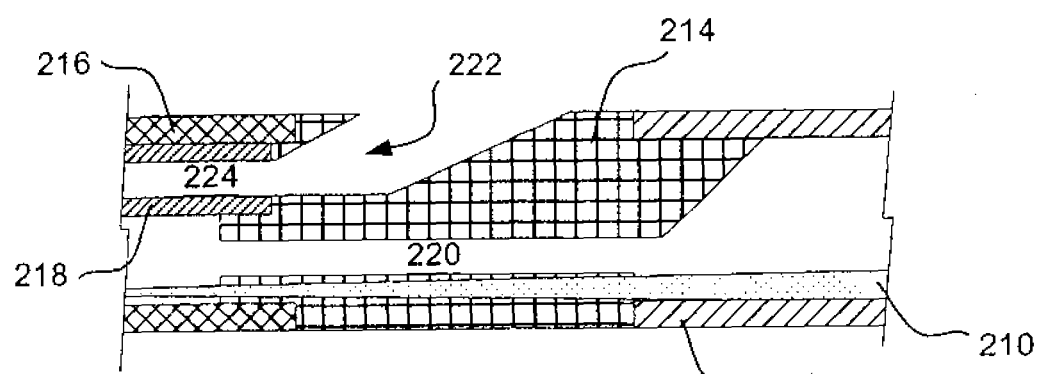

FIG. 6D illustrates the completed distal guidewire port, with the mandrels 202, 208 of FIG. 6C removed. The removal of the inflation mandrel 208 opens an inflation lumen 220 that fluidly connects a lumen in the proximal member 206 to the lumen defined between the distal outer member 216 and the distal inner member 218. The core wire 210 is partly embedded into the member 214, and provides a transition in flexibility and strength from the proximal member 206 across the port joint to the distal members 216, 218. The core wire 210 may be included in similar form in any of the embodiments disclosed herein as an optional strain-relief apparatus.

After the steps illustrated above, and once the devices illustrated in FIGS. 3D, 4D, 5D, and 6D are fabricated, additional steps may be performed to complete the catheter device. In some embodiments the proximal members illustrated may be attached after a proximal hub and/or manifold is provided thereon. In other embodiments, the proximal members may be attached to additional proximal members to reach the proximal end, or a hub or manifold may be directly provided on the proximal members. Additional coatings may also be applied. The distal members, in several embodiments, are provided with a balloon. In one such embodiment, a balloon is attached by any suitable process in a manner such that the balloon has a proximal end attached to the distal outer member and a distal end attached to the distal inner member, and the inflation lumen opens into the balloon.

In further embodiments, multi-lumen proximal or distal members may be used. In several such embodiments, a distal member is used having more lumens than a proximal member. Further, while the Figures illustrate the use of a single lumen proximal section with a dual lumen distal section, other embodiments can include the provision of a dual lumen proximal and triple lumen distal, or any other combination.

Some embodiments include a guidewire path mandrel permanently affixed to a side of the mold, shaped for providing the guidewire entry port, with the mandrel having a distally extending tapered portion which begins at a diameter that is greater than the inner diameter of the distal inner member and ends at a diameter which is less than the inner diameter of the distal inner member, such that the distal inner member may slide over part of the mandrel but can only slide a certain distance up the mandrel. One such embodiment is shown in FIGS. 3A-3D. This allows an easily repeatable fabrication process, since the distal inner member will repeatably slide to the same location on the mandrel. The mandrel may include a ridge or other defined line instead of a smooth taper in another embodiment. The mold may include a mechanism such as a cinch screw, or other elastic or resilient mechanism for holding the distal or proximal members in place once it is advanced to a desired location in the mold. The mandrels may also include one or more mechanisms such as a hook or other device which may protrude from a distal portion of the taper to "catch" the inner wall of the distal inner member.

For the purposes of disclosure, several of the mandrels illustrated herein are shown as generally cylindrical. In several embodiments, various non-cylindrical mandrels may be used including, for example, flattened or crescent-shaped mandrels. In several embodiments, a crescent-shaped mandrel having a flattened end is used to extend through the proximal member into the port joint. The flattened end can be shaped to partially curve around and receive the distal inner member from within the distal outer member. When a crescent-shaped mandrel is used, the inflation lumen may have a circular profile within the proximal member, transition to a crescent-shaped lumen through the port joint, and again transition to an annular lumen distal of the port joint.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of making a catheter, the method comprising:
forming a port joint having a proximal end and a distal end, the port joint including an inflation lumen extending from the proximal end to the distal end of the port joint, the port joint including a guidewire lumen extending from the distal end to a guidewire port located intermediate the proximal end and the distal end of the port joint, the guidewire lumen of the port joint defined by an interior surface of the port joint fully surrounding a periphery of the guidewire lumen;
joining a proximal shaft section of the catheter to the proximal end of the port joint such that a lumen of the proximal shaft section is in fluid communication with the inflation lumen of the port joint; and
joining a distal shaft section of the catheter to the distal end of the port joint such that a first lumen of the distal shaft section is in fluid communication with the inflation lumen of the port joint and a second lumen of the distal shaft section is in fluid communication with the guidewire lumen of the port joint;
wherein the port joint is formed of a material discrete from materials forming the proximal shaft section and the distal shaft section.

2. The method of claim 1, wherein the proximal shaft section is spaced away from the distal shaft section by the port joint.

3. The method of claim 1, wherein the distal shaft section includes an inner tubular member and an outer tubular member surrounding the inner tubular member.

4. The method of claim 3, wherein the second lumen of the distal shaft section is defined by the inner tubular member, and the first lumen of the distal shaft section is defined between the inner tubular member and the outer tubular member.

5. The method of claim 1, wherein the step of forming the port joint includes injection molding polymeric material in a mold.

6. The method of claim 5, wherein the distal shaft section of the catheter is joined to the port joint during formation of the port joint.

7. The method of claim 6, wherein the proximal shaft section of the catheter is joined to the port joint during formation of the port joint.

8. The method of claim 1, wherein the proximal end of the port joint extends into the lumen of the proximal shaft section of the catheter.

9. The method of claim 1, wherein the distal end of the port joint extends into the first lumen of the distal shaft section of the catheter.

10. The method of claim 1, wherein the distal end of the port joint extends into the second lumen of the distal shaft section of the catheter.

11. A method of making a catheter, the method comprising:
providing a proximal tubular member of a catheter shaft, the proximal tubular member having a proximal end, a distal end, and a lumen extending therethrough;
providing a first distal tubular member of the catheter shaft, the first distal tubular member having a proximal end, a distal end, and a lumen extending therethrough;
providing a second distal tubular member of the catheter shaft, the second distal tubular member having a proximal end, a distal end, and a lumen extending therethrough,
wherein both of the first and second distal tubular members are structurally distinct from the proximal tubular member;
providing a port joint for coupling the proximal tubular member of the catheter shaft to the first and second distal tubular members of the catheter shaft, the port joint adapted to couple the lumen of the proximal tubular member to the lumen of the first distal tubular member;
the port joint including:
a) a guidewire lumen disposed within the port joint for directing a guidewire into the lumen of the second distal tubular member, the guidewire lumen defined by an interior surface of the port joint fully surrounding a periphery of the guidewire lumen; and
b) a guidewire port for receiving a guidewire through an exterior wall of the port joint into the guidewire lumen, the guidewire port located intermediate a proximal end and a distal end of the port joint;

attaching the port joint to the distal end of the proximal tubular member of the catheter shaft; and attaching the port joint to the proximal ends of the first and second distal tubular members of the catheter shaft.

12. The method of claim 11, wherein the port joint comprises material that does not come from either the proximal member or the distal members.

13. The method of claim 11, wherein the proximal tubular member is separated from the first and second distal tubular members by the port joint.

14. The method of claim 11, wherein the port joint further includes a proximal portion and a distal portion, and the distal portion is at least partially disposed within the proximal end of at least one of the first distal tubular member and the second distal tubular member.

15. The method of claim 11, wherein the port joint is constructed during a molding process.

16. A method of making a catheter shaft, the method comprising:

providing a port joint for coupling a proximal member of a catheter shaft to one or more distal members of the catheter shaft that are structurally distinct from the proximal member, the port joint adapted to couple a lumen in the proximal member to a first lumen defined by the distal member(s);

the port joint including:

a) a guidewire lumen disposed within the port joint for directing a guidewire into a second lumen defined by the distal member(s), the guidewire lumen defined by an interior surface of the port joint fully surrounding a periphery of the guidewire lumen; and b) a guidewire port for receiving a guidewire through an exterior wall of the port joint into the guidewire lumen, the guidewire port located intermediate a proximal end and a distal end of the port joint;

attaching the port joint to a distal end of the proximal member of the catheter shaft; and attaching the port joint to a proximal end of the one or more distal members of the catheter shaft;

wherein the distal end of the proximal member of the catheter shaft is proximal of the proximal end of the one or more distal members of the catheter shaft, and the distal end of the proximal member of the catheter shaft is longitudinally separated from the proximal end of the one or more distal members of the catheter shaft by the port joint;

wherein the formed catheter shaft includes the proximal member, the port joint, and the one or more distal members.

17. The method of claim 16, wherein the port joint is attached to the distal end of the proximal member of the catheter shaft contemporaneously with molding the port joint in a mold.

18. The method of claim 16, wherein the port joint is attached to the proximal end of the one or more distal members of the catheter shaft contemporaneously with molding the port joint in a mold.

19. The method of claim 16, wherein the port joint comprises material that does not come from either the proximal member or the distal member(s).

20. The method of claim 16, wherein a distal portion of the port joint is at least partially disposed within either the first or second lumen of the distal member(s).

* * * * *